(12) United States Patent
Wang et al.

(10) Patent No.: US 7,879,006 B2
(45) Date of Patent: Feb. 1, 2011

(54) INJECTION AID FOR ANTERIOR JUXTASCLERAL DEPOT

(75) Inventors: Wan-Heng Wang, Fort Worth, TX (US); Liezhi Liang, Grand Prairie, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 154 days.

(21) Appl. No.: 12/357,660

(22) Filed: Jan. 22, 2009

(65) Prior Publication Data

US 2009/0192458 A1   Jul. 30, 2009

(51) Int. Cl.
*A61M 5/00* (2006.01)
(52) U.S. Cl. ..................................... 604/117
(58) Field of Classification Search ............ 604/22, 604/116–117, 521; 600/398–406, 235–236, 600/226; 606/107; 351/201
See application file for complete search history.

(56) References Cited

U.S. PATENT DOCUMENTS

| 4,292,970 | A | | 10/1981 | Hession, Jr. |
| 4,627,841 | A | | 12/1986 | Dorr |
| 5,201,742 | A | * | 4/1993 | Hasson ...................... 606/130 |
| 5,417,209 | A | * | 5/1995 | Morrison ................... 600/398 |
| 2007/0197491 | A1 | | 8/2007 | Robin et al. |
| 2008/0125406 | A1 | | 5/2008 | Robin et al. |

FOREIGN PATENT DOCUMENTS

WO      01/49226 A1    7/2001

* cited by examiner

*Primary Examiner*—Nicholas D Lucchesi
*Assistant Examiner*—Melissa A Snyder
(74) *Attorney, Agent, or Firm*—W. David Lee

(57) ABSTRACT

The present invention is an ophthalmic injection aid having a positioning member and a needle assembly. The injection aid facilitates the creation of an anterior juxtascleral depot of an ophthalmic drug.

4 Claims, 3 Drawing Sheets

INJECTION AID FOR ANTERIOR JUXTASCLERAL DEPOT

This application claims the priority of U.S. Provisional Application No. 61/062,403 filed Jan. 25, 2008.

FIELD OF THE INVENTION

The present invention generally pertains to injection aids. More particularly, but not by way of limitation, the present invention pertains to injection aids for the delivery of ophthalmic drugs via the anterior juxtascleral depot route of administration.

DESCRIPTION OF THE RELATED ART

"Glaucomas" are a group of debilitating eye diseases that are the leading cause of irreversible blindness in the United States in blacks and Hispanics, the second leading cause of blindness in whites in the United States, and a leading cause of blindness in all countries, including both developed and less developed nations. The disease is estimated to affect between 0.4% and 3.3% of all adults over 40 years old (Leske, M. C. et al. (1983); Bengtsson, B. (1989); Strong, N. P. (1992)). Moreover, the prevalence of the disease rises with age to 9.49% in whites and 23.2% in blacks 75 years or older (Friedman, D. S. et al., (2006)). It is estimated that by 2010, 60.5 million people worldwide will be affected with open angle glaucoma and angle closure glaucoma, increasing to 79.6 million by 2020. (Quigley and Broman (2006)). In all glaucomas, eye pressure lowering is strongly associated with a decrease in the rate of developing the disease and a decrease in the rate of progression towards both disability and blindness. Lowering of the eye's pressure, referred to as "the intraocular pressure" (IOP), is the only known way of successfully treating this disease. We know that for every 1 mm Hg decrease in IOP, the chances of progressive damage decrease by approximately 10%. (Leske, M. C., (2003)).

The etiology of glaucoma is still the subject of much research in the U.S. and other countries. Although the causes of the disease are still not entirely clear, it is known that the trabecular meshwork of the eye plays a key role in this disease, particularly with respect to the maintenance of fluid dynamics within the eye. Specifically, if the trabecular meshwork does not function as well as it should, this malfunction leads to a relative obstruction of the normal ability of aqueous humor to leave the eye and an elevation of IOP, resulting in progressive visual loss, visual disability, and blindness, if not treated appropriately and in a timely fashion.

Drugs for the treatment of glaucoma are typically administered topically via eyedrops or orally via pills. In addition, a new method of administration called anterior juxtascleral depot has been developed. The anterior juxtascleral depot route of administration involves injecting a drug into the anterior segment of the eye, outside of the limbus, and below the conjunctiva. U.S. Patent Application Publication No. 2007/0197491 and U.S. patent application Ser. No. 11/778,538 provide additional detail regarding the anterior juxtascleral depot route of administration and are incorporated herein by reference.

Certain challenges and risks are associated with ophthalmic injections. Such challenges and risks include the ability of a patient to hold his or her eye open and in a fixed position during the injection, the ability of the surgeon to properly locate and administer the injection, and the risk of penetrating the globe of the eye due to improper surgical technique. Therefore, a need exists in the ophthalmic field for improved methods and apparatus for ophthalmic injections.

SUMMARY OF THE INVENTION

In one aspect, the present invention is an ophthalmic injection aid including a positioning member and a needle assembly. The positioning member has a body with an upper lid speculum, a lower lid speculum, an eye guide, and a socket aperture. The positioning member also includes a ball and socket hinge assembly. The ball and socket hinge assembly is removably disposed in the socket aperture and has a ball and socket hinge with a central bore and a depth limiter. The needle assembly has a needle on a distal end and a handle on a proximal end. The needle assembly is removably and slidably disposed within the central bore of the ball and socket hinge.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

Figure 1:
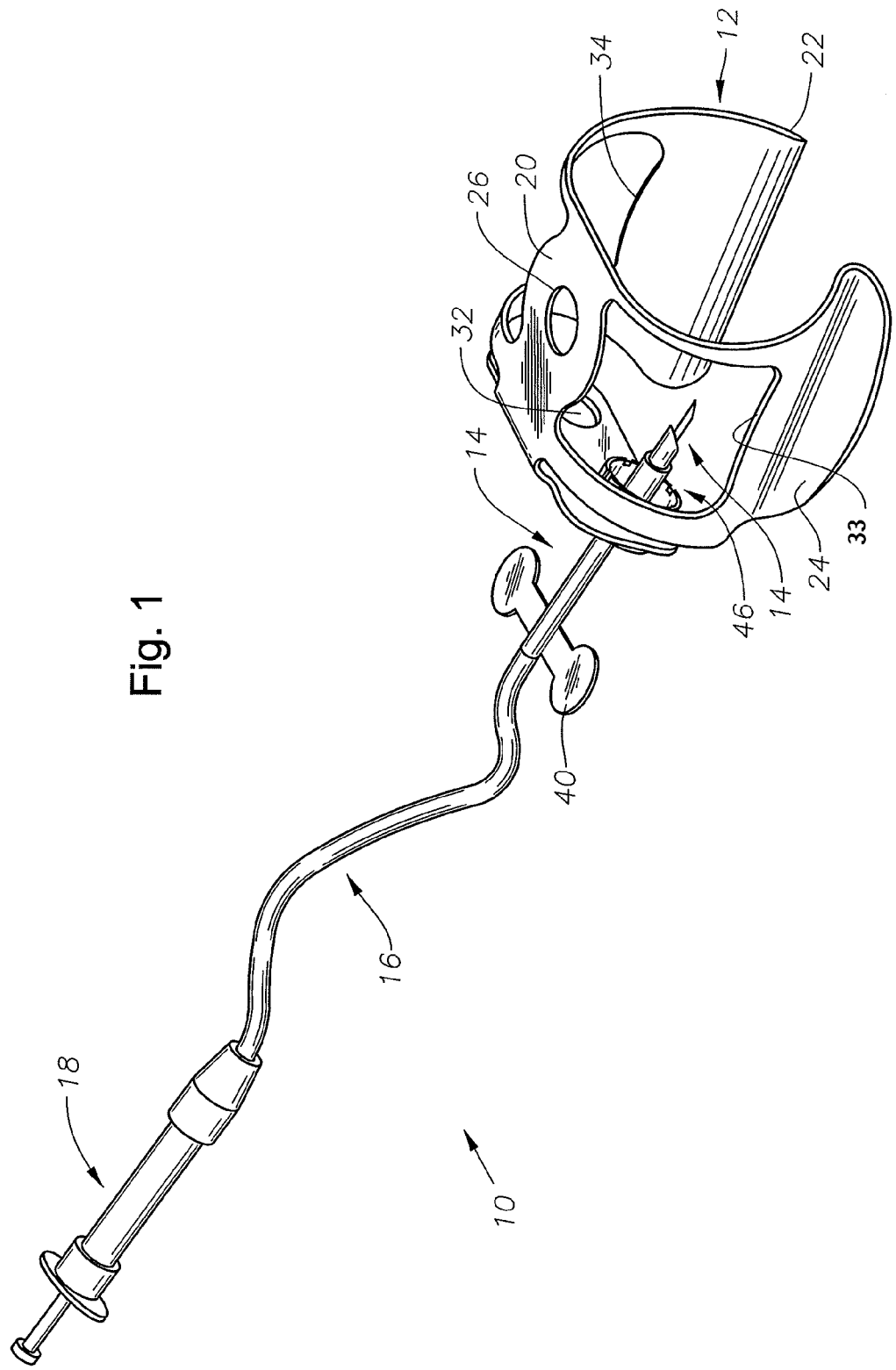
FIG. 1 is a schematic, perspective view of an ophthalmic injection aid according to a preferred embodiment of the present invention.
Figure 2:
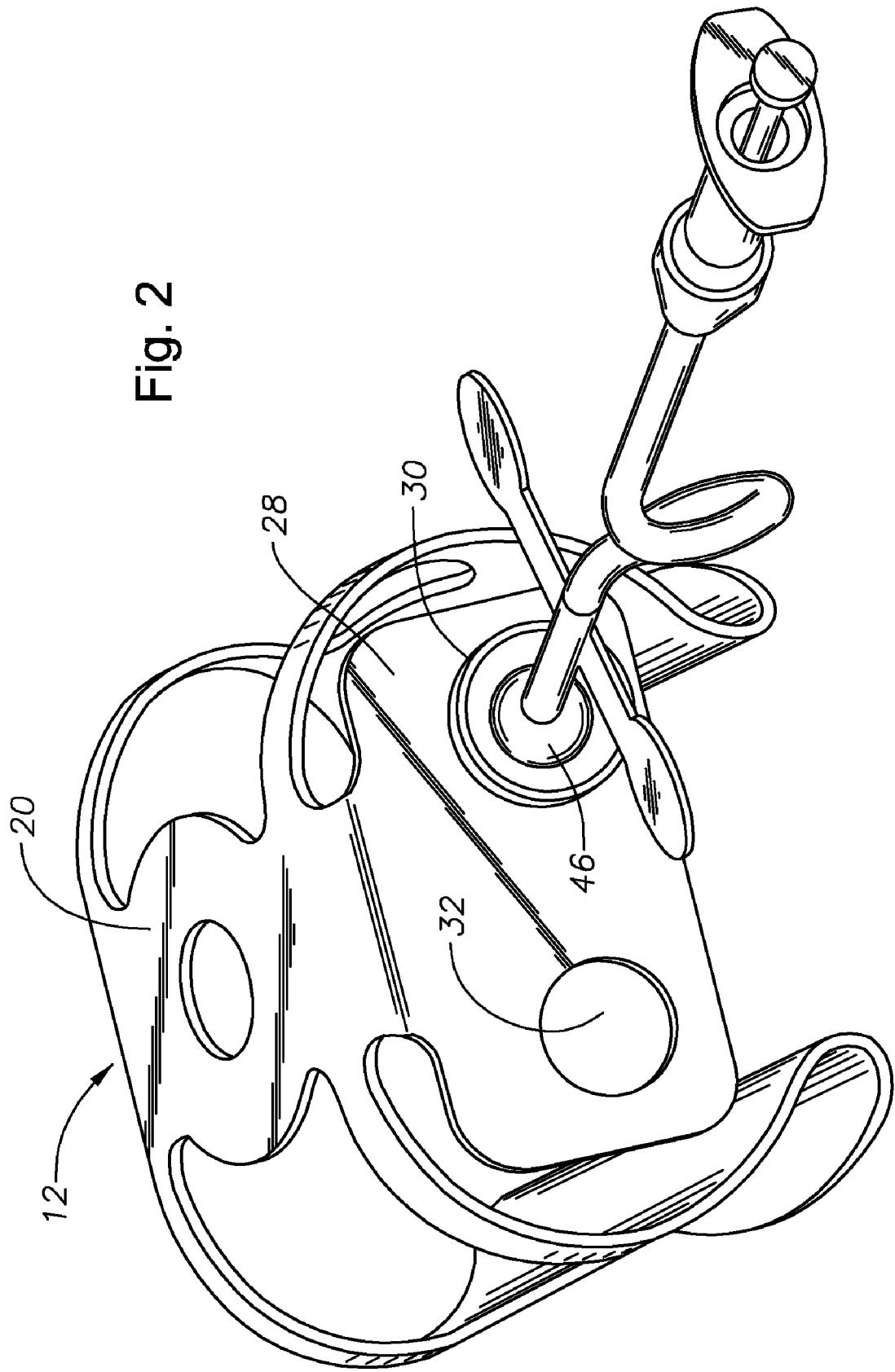
FIG. 2 is a rear, perspective view of the positioning member of the injection aid of FIG. 1.
Figure 3:
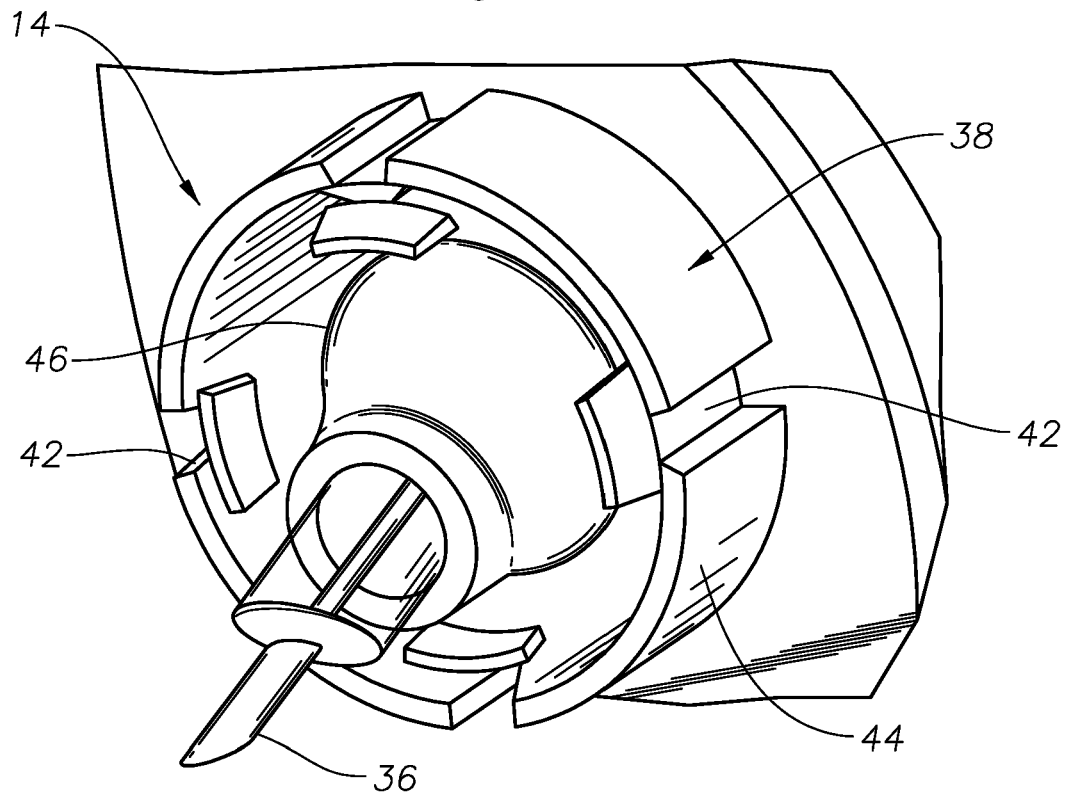
FIG. 3 is an enlarged, front, perspective view of a portion of the positioning member of the injection aid of FIG. 1.
Figure 4:
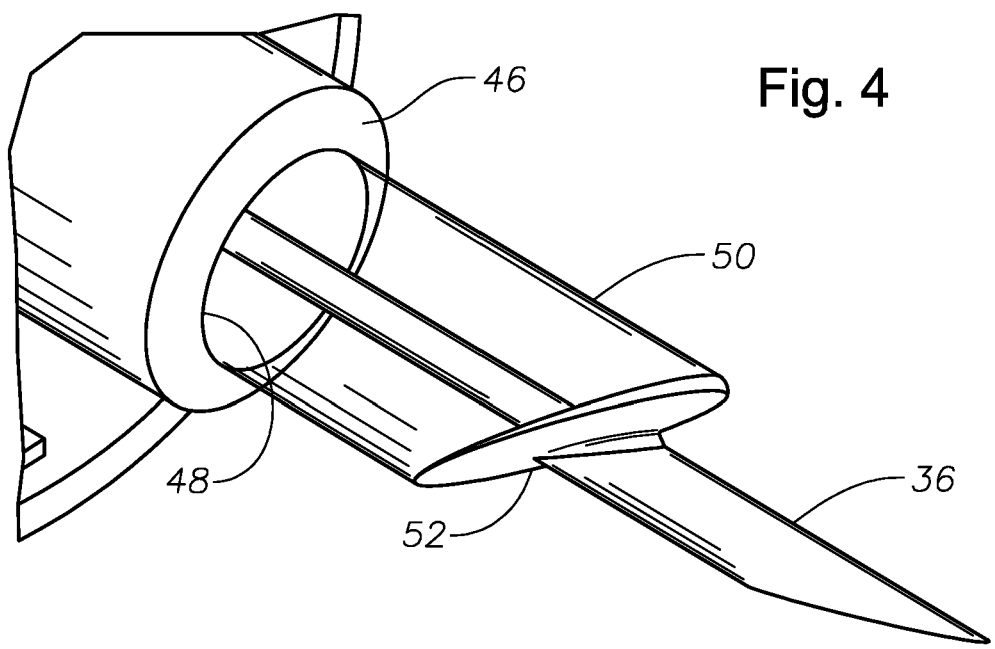
FIG. 4 is an enlarged, front, perspective view of the needle assembly of the positioning member of the injection aid of FIG. 1.

The preferred embodiments of the present invention and their advantages are best understood by referring to FIGS. 1 through 4 of the drawings, like numerals being used for like and corresponding parts of the various drawings. Injection aid 10 generally includes a positioning member 12, a needle assembly 14, tubing 16, and a syringe 18. Positioning member 12 generally includes a body 20 having an upper lid speculum 22, a lower lid speculum 24, an eye guide 26, and a temporal plate 28 with an upper socket aperture 30 and a lower socket aperture 32. Body 20 can be designed with various widths between lid speculum 22 and lid speculum 24 for different size eyes. Body 20 is preferably made from a transparent plastic to increase surgeon visibility to a patient's eye. Body 20 may also be formed with windows 33 and 34 to further increase surgeon visibility. Needle assembly 14 generally includes a needle 36 and a ball and socket hinge assembly 38. Needle 36 is preferably a self-sealing, 30 gage needle having a butterfly handle or base 40. Ball and socket hinge assembly 38 is removably coupled to one of socket apertures 30 or 32 via grooves 42 in a base 44. Grooves 42 are designed to mate with corresponding flanges (not shown) disposed around the periphery of socket apertures 30 and 32. Ball and socket hinge assembly 38 further includes a ball and socket hinge 46 having a central bore 48 and a depth limiter 50 on its distal end. Needle 36 is removably and slidably disposed within central bore 48. A seal 52 fluidly seals needle 36 within depth limiter 50. Tubing 16 is preferably conventional surgical tubing with an internal diameter selected to minimize the amount of drug held within the tubing while providing adequate drug flow. Tubing 16 is removably and fluidly coupled to needle assembly 14 on one end and syringe 18 on another end via conventional means such as a luer-lock. Syringe 18 is preferably a conventional syringe suitable for ophthalmic injections.

During use of injection aid 10, a nurse (or other user) draws the appropriate amount of drug into syringe 18 and tubing 16 using needle assembly 14. The nurse then secures ball and socket hinge assembly 38 within the desired one of socket apertures 30 (superior temporal injection) or 32 (inferior temporal injection). The nurse grasps butterfly handle 40 and inserts needle 36 partially into bore 48 so that the distal tip of needle 36 does not extend from depth limiter 50. The physician (or other user) anesthetizes the patient's eye using conventional topical anesthetic drops. The physician places positioning member 12 upon a patient's eye. Lid speculums 22 and 24 keep the patient's eyelids retracted. The physician instructs the patient to maintain focus through eye guide 26. The physician uses butterfly handle 40 and ball and socket hinge 46 to appropriately position needle 36 for entry into the eye. Preferably, such entry is 3 to 5 mm posterior to the limbus. At this point, depth inserter 50 is just touching or very near the surface of the eye. Once needle 36 is appropriately positioned, the surgeon pushes on butterfly handle 40 to slide needle 36 further into bore 48 so that a distal tip of needle 36 is appropriately positioned within the anterior segment of the eye. The distal tip of needle 36 is preferably positioned below the conjunctiva of the eye, and is most preferably positioned below the Tenon's capsule and above the sclera of the eye. At this point, depth inserter 50 is touching the surface of the eye so that the surgeon has an indication that the distal tip of needle 36 is at the appropriate depth. The surgeon or nurse then uses syringe 18 to slowly inject a drug through needle 18 into the eye. Such injection typically takes 30 to 90 seconds. Preferably, such injection creates an anterior juxtascleral depot of drug within the eye. Once the injection is complete, the surgeon preferably maintains pressure on the outer surface of the eye with seal 52 for a short time period. The contact of seal 52 with the surface of the eye functions to minimize or prevent leaking or reflux of the drug from the depot. The surgeon then uses butterfly handle 40 to withdraw needle 36 from the eye so that the distal tip of the needle is not extending from depth limiter 50. Since syringe 18 is remote from needle assembly 14, there is no risk of patient injury due to actuation of the syringe plunger or inadvertent movement of the syringe.

From the above, it may be appreciated that the present invention increases the ability of a patient to hold his or her eye open and in a fixed position during an injection, increases the ability of the surgeon to properly locate and administer the injection, decreases the risk of penetrating the globe of the eye due to improper surgical technique, and minimizes or eliminates leaking or reflux of the injected drug.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An ophthalmic injection aid, comprising:
    a positioning member having:
        a body with an upper lid speculum, a lower lid speculum, an eye guide, and a socket aperture, said upper lid speculum having a first curved surface to engage an upper eyelid of a patient and to keep said upper eyelid retracted, said lower lid speculum having a second curved surface to engage a lower eyelid of said patient and to keep said lower eyelid retracted; and
        a ball and socket hinge assembly removably disposed in said socket aperture, said ball and socket hinge assembly having a ball and socket hinge with a central bore and a depth limiter; and
    a needle assembly having a needle on a distal end and a butterfly handle on a proximal end, said needle assembly being removably and slidably disposed within said central bore of said ball and socket hinge.

2. The ophthalmic injection aid of claim 1 wherein said depth limiter limits a depth of insertion of a distal tip of said needle into an eye.

3. The ophthalmic injection aid of claim 1 further comprising:
    a syringe; and
    tubing having a distal end and a proximal end, said distal end of said tubing being removably and fluidly coupled to said handle, and said proximal end of said tubing being removably and fluidly coupled to said syringe.

4. The ophthalmic injection aid of claim 1 wherein said body comprises a second socket aperture, wherein said socket aperture is for facilitating a superior temporal ophthalmic injection and said second socket aperture is for facilitating an inferior temporal ophthalmic injection.

* * * * *